United States Patent
Grundei

(10) Patent No.: US 7,018,420 B2
(45) Date of Patent: Mar. 28, 2006

(54) SUBCUTANEOUS, INTRAMUSCULAR BEARING FOR A RIGID TRANSCUTANEOUS IMPLANT

(75) Inventor: Hans Grundei, Lübeck (DE)

(73) Assignee: ESKA Implants GmbH & Co., Lübeck (DE)

(*) Notice: Subject to any disclaimer, the term of this patent is extended or adjusted under 35 U.S.C. 154(b) by 0 days.

(21) Appl. No.: 10/983,204

(22) Filed: Nov. 5, 2004

(65) Prior Publication Data
US 2005/0102038 A1 May 12, 2005

(30) Foreign Application Priority Data
Nov. 7, 2003 (DE) .............................. 103 53 400
Feb. 18, 2004 (DE) ...................... 10 2004 008 558

(51) Int. Cl.
A61F 2/60 (2006.01)
A61F 2/78 (2006.01)
(52) U.S. Cl. ..................................................... 623/32
(58) Field of Classification Search ............. 623/23.44, 623/23.45, 23.46, 32
See application file for complete search history.

(56) References Cited
U.S. PATENT DOCUMENTS 3,947,897 A * 4/1976 Owens ..................... 623/11.11
4,158,895 A 6/1979 Frosch et al.
6,843,808 B1 * 1/2005 Grundei ........................ 623/32
6,869,450 B1 * 3/2005 Grundei ........................ 623/32

FOREIGN PATENT DOCUMENTS

| DE | 37 04 089 C2 | 10/1990 |
| DE | 100 40 590 A1 | 3/2002 |
| DE | 102 47 397 B3 | 1/2004 |
| DE | 102 30 074 B3 | 4/2004 |
| EP | 1 378 215 A1 | 1/2004 |
| EP | 1 407 727 A1 | 4/2004 |

* cited by examiner

Primary Examiner—Bruce Snow
(74) Attorney, Agent, or Firm—Akin Gump Strauss Hauer & Feld, LLP

(57) ABSTRACT

A subcutaneous, intramuscular bearing (1) for a rigid transcutaneous implant (2) is provided, for anchoring intracorporally in a bone stump and having an intermediate piece (3) between the implant (2) and an extracorporal coupling for coupling on the implant. A rigid bushing (5) is tightly connected to the intermediate piece (3), such that between the wall of the bushing (5) and the intermediate piece (3) an annular space (6) is formed, which is closed in the intracorporal direction, for receiving and setting the extracorporal coupling. The outer wall of the bushing (5) has an openmeshed, three-dimensional lattice structure (8) and a lattice-free distal region having a width B. A spring ring (9) is set in the annular space (6) from the distal end, moved with a telescoping motion, and locked under exertion of its spring effect.

15 Claims, 5 Drawing Sheets

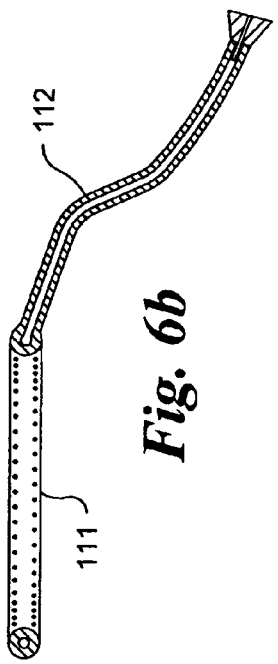
Fig. 6a
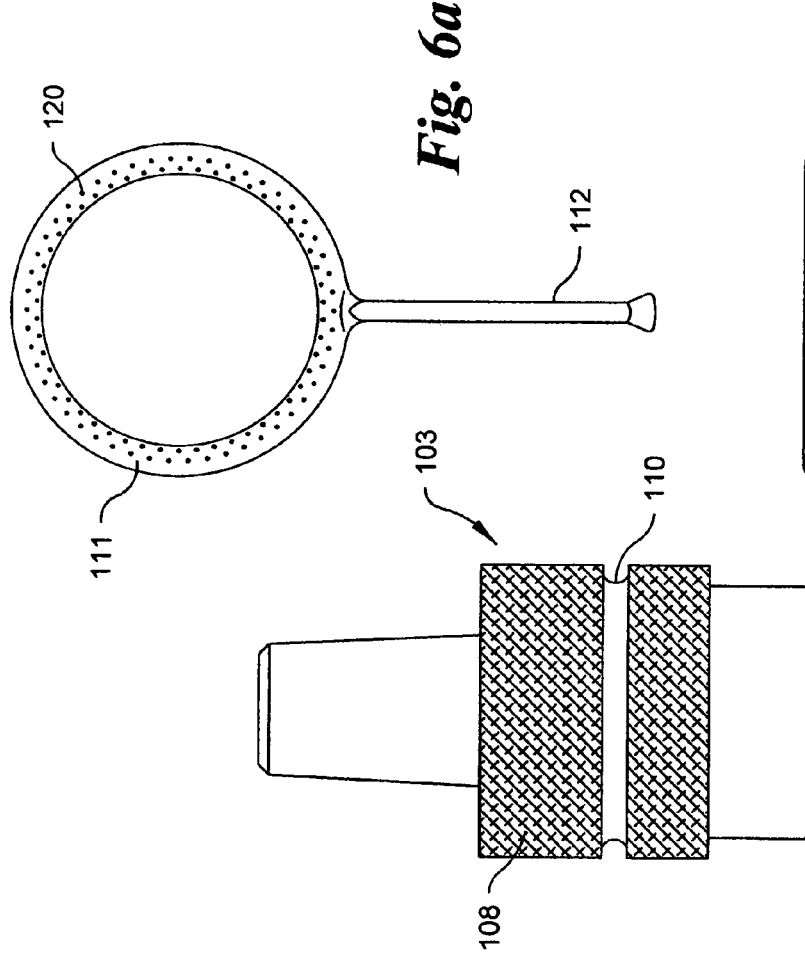
Fig. 6b
Fig. 5
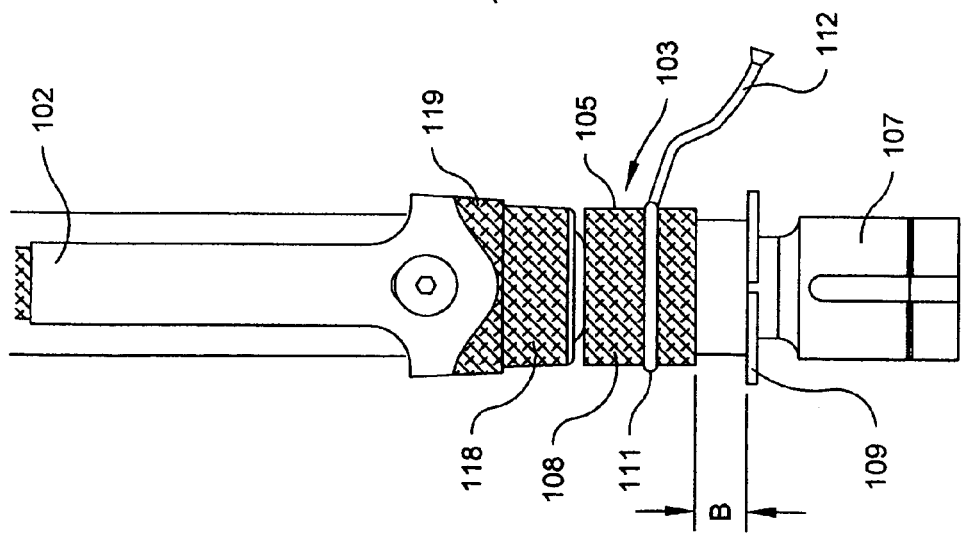
Fig. 4

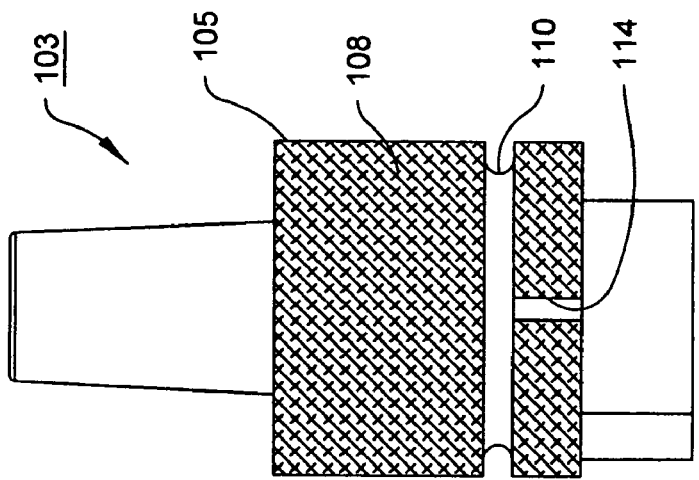
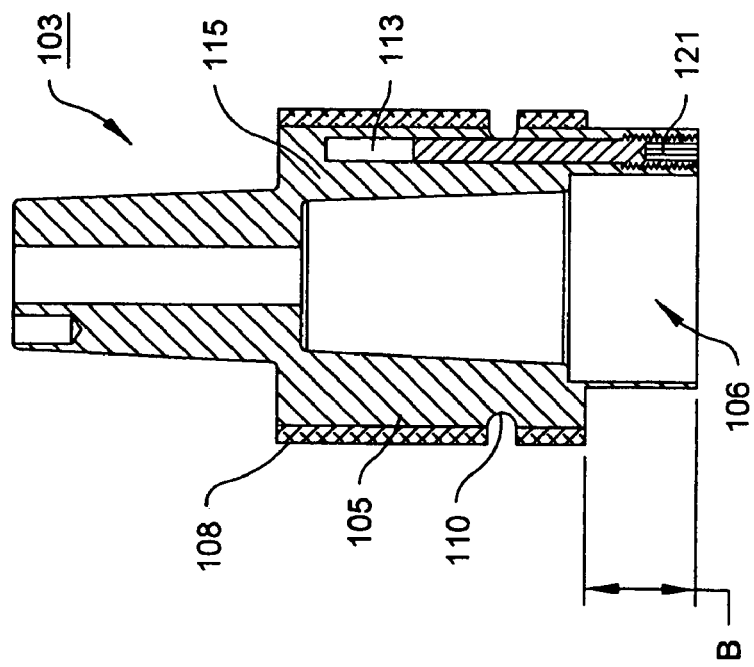
Fig. 7a
Fig. 7b

SUBCUTANEOUS, INTRAMUSCULAR BEARING FOR A RIGID TRANSCUTANEOUS IMPLANT

BACKGROUND OF THE INVENTION

The invention relates to a subcutaneous, intramuscular bearing for a rigid transcutaneous implant, which can be anchored intracorporally in a bone stump and which has an intermediate piece between the implant and an extracorporal coupling that can be coupled to this intermediate piece.

Such a bearing is known from German published patent application DE 100 40 590 A1. The bearing described in this publication comprises a flexible material and it has a bushing, which closely surrounds the implant distally. The bearing also has an intracorporally arranged coupling sleeve in the form of flexible pleated bellows, which is proximally connected to the bushing in a sealed manner with a molded collar, such that a hollow space of a minimum width remains free between the inner wall of the pleated bellows and the outer wall of the bushing. In this way, a flexible lattice network is arranged distally on the pleated bellows and is connected on the distal end to another lattice network with a higher modulus of elasticity.

With this bearing, the goal is achieved that soft parts can move relative to the rigid implant without exposing the point in the body-part stump where the implant emerges to an increased risk of inflammation.

Even if this known bearing is successfully inserted in practice, there is the risk that in the case, for example, when the point where the implant emerges through the thigh stump is cleaned with a hollow needle, the flexible material, in most cases silicone, is also pierced and a contamination occurs.

BRIEF SUMMARY OF THE INVENTION

Against this background, it is now an object of the present invention to improve a conventional subcutaneous, intramuscular bearing of the type mentioned at the outset, such that safety against contamination of the point in the body where the implant emerges (emergence point) and the adjacent regions of the thigh stump is significantly increased, and inadvertent removal of the germ barrier is prevented.

Accordingly, it is proposed according to a first embodiment that the bearing have a rigid bushing firmly connected to the intermediate piece, and that, between the wall of the bushing and the intermediate piece, an annular space be provided, which is closed in the intracorporal direction and in which the extracorporal coupling can be set. On the outer wall of the bushing there is an open-meshed, three-dimensional lattice structure, except for a region maintained in the distal region having a width B, preferably of up to about 2 cm. Furthermore, a spring ring is provided, which can be set into the annular space from the distal end, which can move with a telescoping motion, and which can be locked under exertion of its spring force.

Relative to the known bearing, the present bushing is a rigid element, which cannot be pierced, e.g., by hollow injection needles. The open-meshed, three-dimensional lattice structure provided on the outer wall of the bushing serves to allow connective tissue to form a structure therein and thus form a germ barrier. The distal region remains free from the three-dimensional lattice structure to allow movement of the surrounding connective tissue for compensating movements.

The spring ring is pressed together, for example with a spring chuck, and inserted into the annular space and pushed in, so that the layer of connective tissue starting at the end of the three-dimensional lattice structure on the bushing bridges over up to the skin of the thigh stump. The adjustability is tailored according to patient-specific conditions.

The surgery now proceeds so that, after the amputation of the thigh, the transcutaneous implant is first anchored in the bone stump, and the distal end is provided with the intermediate piece. Then, the thigh stump is closed until the transcutaneous implant has grown into the bone stump. Finally, after approximately 6 to 8 weeks, the thigh stump is opened with a skin cutting device and the spring ring is pressed together by means of a spring chuck, so that the spring ring can be guided into the annular space.

The spring ring is preferably a bent out ring with a radial slot. The outward flange then lies from the outside against the skin of the thigh stump. The radial slot is used for two purposes: first, the spring ring can be pressed together for insertion into the annular space. After removing the spring chuck, the ring expands in circumference and thereby generates the spring force necessary for the locking. In addition, the radial slot serves for drainage or discharge of internal bodily secretions.

The mesh spacings of the three-dimensional lattice structure on the bushing are preferably about 50 to 2500 μm. These mesh spacings are relatively large, but hold a sufficient amount of connective tissue surrounding the mesh, so that a reliable germ barrier can be produced.

The bushing can be connected firmly to the intermediate piece by heat-shrinking the bushing on the intermediate piece. Alternatively, it can also be fused with the intermediate piece. It is also possible for the bushing to be formed integrally as one piece with the intermediate piece. In each case, it must be guaranteed that the connection between the bushing and the bearing is tight and rigid and can withstand the applied loads.

A second embodiment provides a subcutaneous bearing: having a rigid bushing connected firmly to the intermediate piece with a coupling element, which is closed in the intracorporal direction and to which the extracorporal coupling can be coupled; having an open-meshed, three-dimensional lattice structure on the outer wall of the bushing while maintaining a free width B in the distal region; having an activatable device provided in the region where the implant emerges from the leg stump for application of bioactive material; and having a spring ring, which can be set into the coupling element from the distal end, which can move with a telescoping motion, and which can be locked by exerting its spring effect.

The bearing according to this second embodiment differs from that according to the first embodiment essentially by the activatable device provided in the region where the implant emerges from the leg stump for application of bioactive material. In this way, an optimal maintenance or care of the point where the implant emerges from the thigh stump is guaranteed. Here, the term "bioactive material" is understood to mean a medicine.

The critical region where the implant emerges from the thigh stump can thus be medicinally cared for with a view to an improved wound healing effect, but also with a view to a preventive effect against inflammation. The wound healing is greatly improved by the application of medicine.

According to a first preferred form of this second embodiment, the activatable device for application of bioactive material has at least one annular groove formed in the outer wall of the bushing and at least one hollow ring that can be set in the annular groove, the hollow ring being made of elastic and porous material with a molded inlet port, through which the hollow ring can be supplied with liquid bioactive material. Through the inlet port, the bioactive material is fed into the interior of the hollow ring. The material exits this ring over time due to the porosity, wets the regions of the open-meshed implant lying underneath, and then flows down in the direction towards the point where the implant emerges from the thigh stump. The hollow ring represents a certain reservoir. The storage capacity in terms of time is decisively influenced by the porosity of the material, from which it is made. Preferably, this is selected so that bioactive material need only be supplied approximately every week.

In an especially preferred refinement, the hollow ring and the inlet port comprise a silicone. Here, the hollow ring and the inlet port are preferably formed integrally.

According to a second preferred form of the second embodiment, the device for applying the bioactive material includes at least one annular groove formed in the outer wall of the bushing and at least one branch channel arranged laterally next to the coupling element in the bushing, which extends so that it intersects the periphery of the one or more annular grooves. The branch channel(s) serve for applying the bioactive material. After the application of the bioactive material, the branch channel(s) can be re-closed, preferably by a seal, for example by a screw. Therefore, this embodiment is concerned less with the long-term application of the bioactive material than with the instantaneous and short-term supply of material to the point where the implant emerges from the thigh stump.

In one especially preferred refinement of this embodiment, at least one branch channel, particularly preferred three branch channels, extend on the outer wall of the bushing in the lower region of the three-dimensional lattice structure, between the lowermost annular groove and the three-dimensional lattice free region of the bushing, for transporting the bioactive material to the point where the implant emerges from the leg stump.

According to a third concrete preferred form of the second embodiment, an annular space is arranged around the coupling element, in which space a supply of elastic film made from bioactive material is stored. Here, the film emerges from the annular space through an annular slot in the bushing and runs along the three-dimensional lattice structure-free region of the bushing to the point where the implant emerges from the leg stump. Here, it surrounds the bushing like a tube. In the three-dimensional lattice structure-free region, the film adheres to the tissue or skin surrounding it. Due to the growth of the skin and tissue, the film is pulled outwardly, wherein it carries possible germs and bacteria with it. The growth of the tissue and skin equals a maximum of about 1 mm per day. Correspondingly, the film is pulled from the intermediate piece by this measure. Storage times of up to one year for the film supply are possible before the annular space must be charged with a new film supply.

This embodiment is not targeted to an instantaneous short-term wound healing treatment. Instead, here the long-term preventive effect against possible infection is in the foreground.

All of the forms of the bearing according to the second embodiment can be improved even more advantageously by embodying the coupling element as a conical clamping sleeve. This permits a smaller overall size than a double cone, as was described in the scope of the first embodiment. In general, all refinements of the first embodiment can be applied to the second embodiment.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 4 is a schematic side view of a transcutaneous implant with the intermediate piece according to a second embodiment of the invention;

FIG. 5 is an enlarged side view of the intermediate piece of FIG. 4;

FIGS. 6(a) and 6(b) are respectively top view (a) and side view (b) of the hollow ring shown in FIG. 4;

FIGS. 7(a) and 7(b) are respectively a schematic cross-sectional view (a) and a schematic view (b) of the intermediate piece according to the second embodiment.

DETAILED DESCRIPTION OF THE INVENTION

Figure 1:
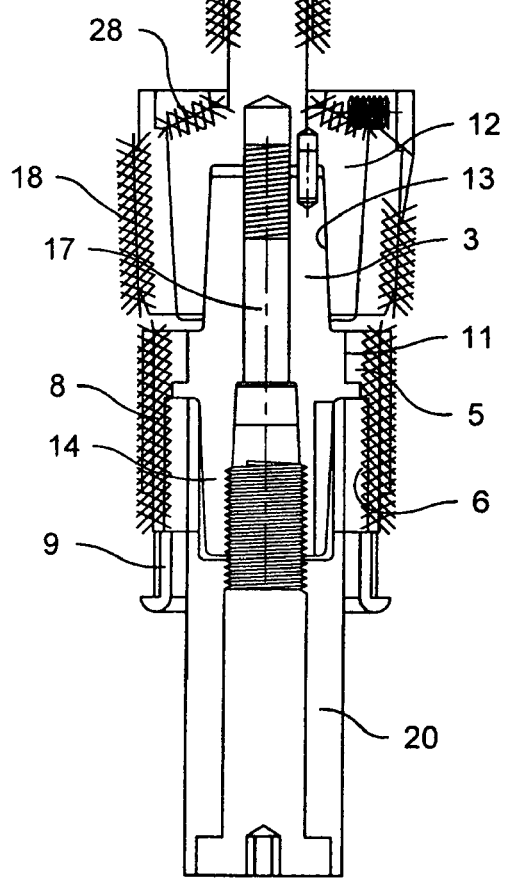
FIG. 1 is a longitudinal sectional view of a subcutaneous, intramuscular bearing, coupled to a transcutaneous implant according to a first embodiment of the invention.
Figure 1:
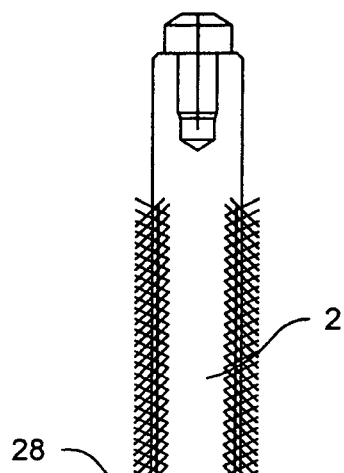

FIG. 1 gives a first overview. A rigid transcutaneous implant 2 is inserted into a femur stump (not shown). The open meshed, three-dimensional lattice structure 28 is used in the present case for integrating bone material for secondary fixation of the implant 2 into the bone. It is sealed on the distal end by a metal sleeve 12, which seals the femur stump. For this purpose, the metal sleeve 12 also carries a three-dimensional, open-meshed lattice structure 28, in which bone material should grow.

In the interior of the metal sleeve 12, a conical clamping sleeve 13 is formed. This is provided for manufacturing a conical clamp connecting with the intermediate piece 3 presently embodied as a double cone. The intermediate piece 3 has a cylindrical center section 11, on which the bushing 5 is heat-shrunk. Another cone 14 connects to the center section 11 on the distal side for producing a conical clamp with a conical clamping sleeve in an adapter of the extracorporal coupling (not shown).

The bushing 5 is formed so that, between its wall and the intermediate piece 3, there is an annular space 6 closed in the intracorporal or proximal direction. In this annular space 6, the extracorporal coupling is set.

Figure 3:
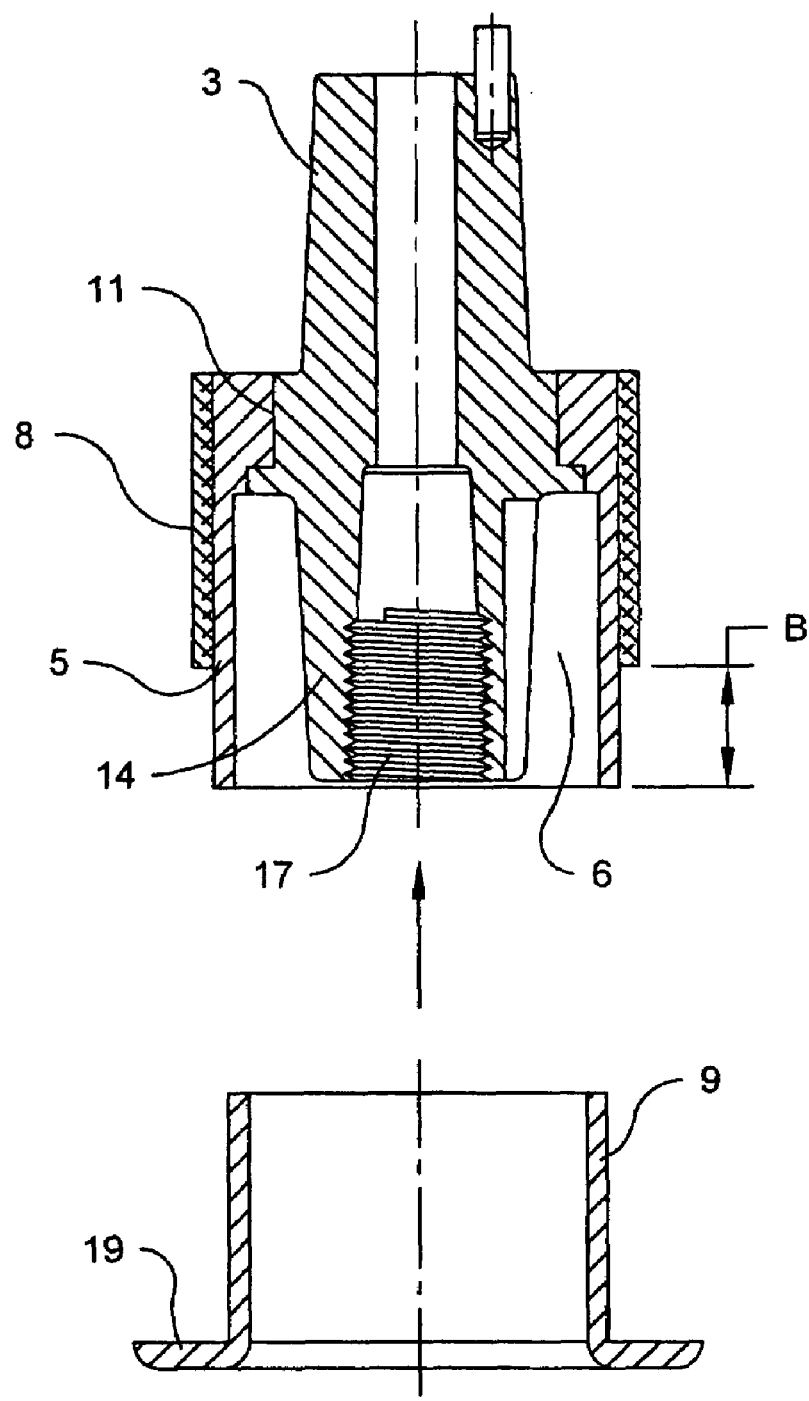
FIG. 3 is an exploded schematic sectional view of an intermediate piece of the bearing with bushing and spring ring.

The outer side of the bushing 5 has in the proximal region an open-meshed, three-dimensional lattice structure 8, into which the connective tissue surrounding the bushing 5 after implantation grows by granulation in order to form a germ barrier. In the distal region of the outer wall of the bushing 5, there is no three-dimensional lattice structure in a region with a width B (FIG. 3). This permits a compensating motion of the surrounding connective tissue without leading to stress in the tissue.

For the implantation, the transcutaneous implant 2 is first implanted in the femur stump with the metal sleeve 12 mounted thereon, and the thigh stump is then closed for setting the implant. After 6 to 8 weeks sufficient bone material has grown into the three-dimensional lattice structure 28 of the implant 2, so that this remains stable even under loads in the femur stump. Simultaneously, connective tissue grows into the three-dimensional lattice structure 18 on the outer wall of the metal sleeve 12 to form a first germ barrier.

After the mentioned time span, the thigh stump is reopened and the intermediate piece 3 with the bushing 5 is guided into the opening in the femur stump and locked there by a conical clamp connection between the double cone and the clamping sleeve 13. An additional securing device 17 (here in the form of a screw) serves for additional securing.

Figure 2:
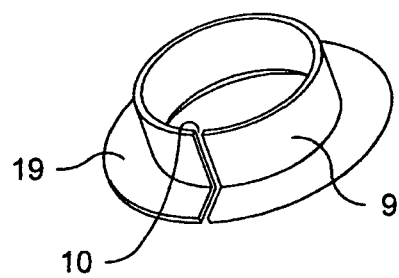
FIG. 2 is a perspective view of an embodiment of the spring ring.

After opening the thigh stump, the spring ring 9 is pressed together by a spring chuck (FIG. 2), wherein the radial slot 10 is provided and inserted into the annular space 6. By telescopic insertion or shifting of the ring 9 in the annular space, the patient-specific distance between the distal end of the bushing 5 and the skin of the thigh stump can be set. The bent flange 19 of the spring ring 9 then contacts the skin of the thigh stump. The slot 10 serves, on the one hand, for the possibility of pressing the spring ring together with a spring chuck in order to generate a spring force when the spring chuck is released and, on the other hand, for discharge of possible bodily secretions.

A measurement bolt 20 is now inserted into the annular space 6. With the help of this bolt, the required length for the extracorporal coupling can be determined.

The relationships are clearly seen again, enlarged in FIG. 3. Here, the intermediate piece 3 with heat-shrunk bushing 5 is shown isolated (exploded view), so that an annular space 6 results between the cone 14 and the bushing 5.

The heat-shrinking of the bushing 5 on the intermediate piece 3 is now especially successful due to the cylindrical center section 11 of the intermediate piece 3. Clearly recognizable is also the open-meshed, three-dimensional lattice structure 8 on the outer wall of the bushing 5, into which the connective tissue, surrounding it after implantation, grows for forming the germ barrier. Shown in FIG. 3 is also the width B, i.e., the width of the region, which is free of a three-dimensional lattice structure 8 on the distal end. From FIG. 3 it can also be seen, based on the indicating arrow, how the clamping ring 9 is inserted into the annular space 6. After finding the correct insertion depth, the spring chuck is then released and the spring ring 9 expands, so that it lies against the inner wall of the bushing 5 and hardens in this position.

FIG. 4 again shows the rigid transcutaneous implant 102, which can be anchored intracorporally in a bone stump. It again has an intermediate piece 103 between the implant 102 and an extracorporal coupling 107 that can be coupled to the implant.

A rigid bushing 105 is connected to the intermediate piece 103. The bushing 105 has a coupling element 106 (FIGS. 7a and 8) closed in the intracorporal direction, to which the extracorporal coupling 107 is coupled.

The outer wall of the bushing 105 again carries an open-meshed, three-dimensional lattice structure 108, in which connective tissue is integrated to form a germ barrier. The metal sleeve 119 closing the implant 102 similarly carries the three-dimensional, open-meshed lattice structure 118 for this same purpose.

An annular ring groove 110 is embedded in the outer wall of the bushing 105, in the embodiment shown. In this annular groove 110, a hollow ring 111 with a connected inlet port 112 is attached. Details of the hollow ring 111 can be seen from FIG. 6.

The inlet port 112 is formed directly on the hollow ring 111. Both preferably comprise silicone. The hollow ring 111 is porous or has small holes 120, from which the supplied bioactive material can emerge and thus can perform its therapeutic effect in the region of the point where the implant emerges from the thigh stump.

FIGS. 7(a) and (b) show a second embodiment of the intermediate piece 103. The bushing 105, again coated with the three-dimensional lattice structure 108, now has an annular ring groove 110. As one can see in the sectional view (FIG. 7a), in the right side of the bushing 105 there is a branch channel 113, which is presently closed with a tightened screw 121. The branch channel 113 is formed in the bushing 105, so that it intersects the periphery of the annular groove 110, so that a bioactive material brought into the branch channel 113 can emerge from the branch channel 113 into the annular groove 110 to perform there its therapeutic effect. For applying the bioactive material, the screw 121 must be unscrewed from the branch channel 113, after which the bioactive material can then be injected into the channel 113, for example with a hollow needle. After successful treatment, the branch channel 113 is re-closed with the screw 121.

So that a good distribution of the bioactive material can take place, three branch channels 114 are now provided (FIG. 7b), which connect the annular groove 110 to the three-dimensional lattice structure region of the bushing 105 with the width B. The bioactive material then flows from the annular groove 110 through the branch channels 114 in the direction of the implant emergenece. point.

Figure 8:
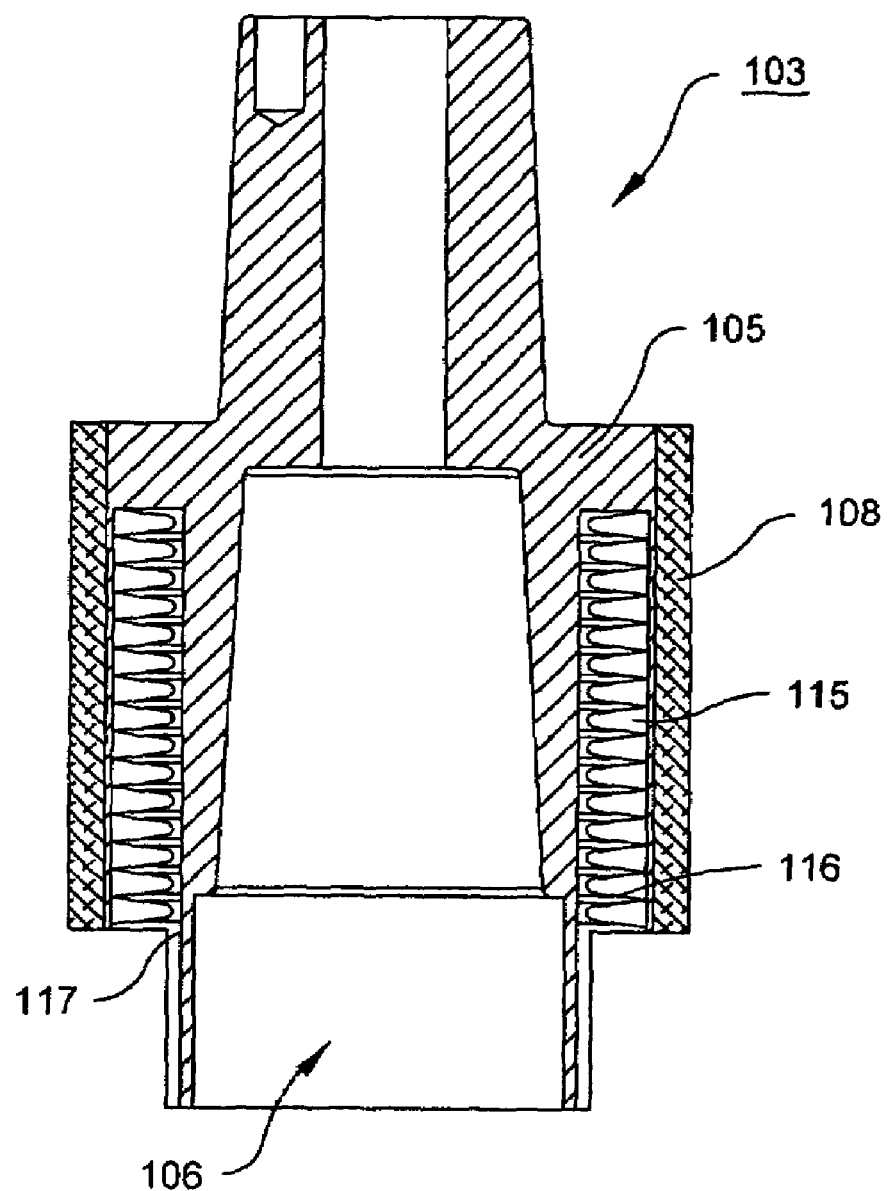
FIG. 8 is a cross-sectional view of the intermediate piece according to a third embodiment.

Finally, FIG. 8 shows the third preferred embodiment of the intermediate piece 103. Here, an annular ring space 115 is formed around the coupling element 106. In the annular space 115, there is a supply of an elastic film 116 made of bioactive material.

The film in the form of a pressed-together tube emerges through a ring-shaped slot 117 from the annular space 115 and then runs along the three-dimensional lattice-free region of the bushing 105 up to the emergence point of the implant from the leg stump. The film 116 here surrounds this section of the sleeve 105 in the shape of a tube. In the bottom region, the film 116 adheres to the surrounding tissue or skin and is pulled outwards with the growth of the skin and the tissue through the region where the implant emerges. In this way, the film carries possible germs outwardly with it. The patient can then cut off the discharged film material 116 from time to time.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A subcutaneous, intramuscular bearing for a rigid transcutaneous implant (2), which can be anchored intracorporally in a bone stump, comprising:
   an intermediate piece (3) between the implant (2) and an extracorporal coupling that can be coupled to the implant
   a rigid bushing (5) tightly connected to the intermediate piece (3), such that between a wall of the bushing (5)

and the intermediate piece (3) a closed annular space (6) is formed in an intracorporal direction to receive the extracorporal coupling, an open-meshed, three-dimensional lattice structure (8) on an outer wall of the bushing (5) and a distal region of the outer wall having a width B which is free of the three-dimensional lattice structure, and a spring ring (9), insertable in the annular space (6) from its distal end, moved there with a telescoping motion, and locked under exertion of a spring effect of the spring ring (9).

2. The bearing according to claim 1, wherein the spring ring (9) comprises a ring having a bent section and a radial slot (10).

3. The bearing according to claim 1, wherein the three-dimensional lattice structure free region of the bushing (5) has a width B of up to about 2 cm.

4. The bearing according to claim 1, wherein the three-dimensional lattice structure has mesh widths in a range of about 500 to 2500 μm.

5. The bearing according to claim 1, wherein the bushing (5) is tightly connected to the intermediate piece (3) by heat-shrinking onto the intermediate piece.

6. The bearing according to claim 1, wherein the bushing (5) is fused with the intermediate piece.

7. The bearing according to claim 1, wherein the bushing (5) is an integral one-piece unit with the intermediate piece (3).

8. The bearing according to claim 1, wherein the intermediate piece (3) comprises a double cone having a cylindrical center section (11) to which the bushing (5) is connected.

9. A subcutaneous, intramuscular bearing for a rigid transcutaneous implant (102), which can be anchored intracorporally in a bone stump, comprising:

an intermediate piece (103) between the implant (102) and an extracorporal coupling (107) that can be coupled to the implant, a rigid bushing (105) tightly connected to the intermediate piece (103) with a coupling element (106), which is closed in an intracorporal direction and to which the extracorporal coupling (107) can be coupled, an open-meshed, three-dimensional lattice structure (108) on an outer wall of the bushing (105) and a distal region of the outer wall having a width B which is free of the three-dimensional lattice structure, an activatable device for applying bioactive material, provided in a region where the implant emerges from the leg stump, and a spring ring (109), insertable in the coupling element (106) from its distal end, moved there with a telescoping motion, and locked under exertion of a spring effect of the spring ring (109).

10. The bearing according to claim 9, wherein the activatable device comprises:

at least one circular ring groove (110) formed in the outer wall of the bushing (105), and at least one hollow ring (111), insertable in the ring groove (110) and comprising an elastic and porous material having a molded inlet port (112), through which the hollow ring (111) can be charged with a liquid bioactive material.

11. The bearing according to claim 10, wherein the material of the hollow ring (111) and the inlet port (112) comprises silicone.

12. The bearing according to claim 9, wherein the activatable device comprises:

at least one circular ring groove (110) formed in the outer wall of the bushing (105), and at least one branch channel (113) arranged laterally in the bushing (105) adjacent the coupling element (106), and extending to intersect a periphery of the at least one ring groove (110) for introducing a liquid bioactive material.

13. The bearing according to claim 12, further comprising at least one branch channel (114) on the outer wall of the bushing (105) in a lower region of the three-dimensional lattice structure (108) between a lowermost ring groove (110) and the three-dimensional lattice structure free region of the bushing (105) for transporting the bioactive material to a point where the implant emerges from the leg stump.

14. The bearing according to claim 9, further comprising an annular ring space (115) arranged around the coupling element (106) and a supply of elastic film (116) comprising bioactive material stored in the annular ring space (115), wherein the film (116) emerges from the annular space (115) through a ring-shaped slot (117) in the bushing (105), extends along the three-dimensional lattice structure free region of the bushing (105) up to a point where the implant emerges from the leg stump, and surrounds the coupling element (106) like a tube.

15. The bearing according to claim 14, wherein the coupling element (106) comprises a conical clamping sleeve.

* * * * *